(12) United States Patent
Brandenburger et al.

(10) Patent No.: US 8,992,490 B2
(45) Date of Patent: Mar. 31, 2015

(54) DRIP CHAMBER FOR AN INFUSION DEVICE AND INFUSION DEVICE HAVING A DRIP CHAMBER

(75) Inventors: Torsten Brandenburger, Reichelsheim (DE); Ismael Rahimy, Friedberg (DE)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 638 days.

(21) Appl. No.: 13/266,017

(22) PCT Filed: May 18, 2010

(86) PCT No.: PCT/EP2010/003038
§ 371 (c)(1),
(2), (4) Date: Oct. 24, 2011

(87) PCT Pub. No.: WO2010/133343
PCT Pub. Date: Nov. 25, 2010

(65) Prior Publication Data
US 2012/0046619 A1    Feb. 23, 2012

(30) Foreign Application Priority Data
May 22, 2009    (DE) .......................... 10 2009 022 417

(51) Int. Cl.
*A61M 5/14* (2006.01)
*A61M 5/38* (2006.01)

(52) U.S. Cl.
CPC .............. *A61M 5/38* (2013.01); *A61M 5/1411* (2013.01)
USPC ............................. 604/251; 604/415; 604/416

(58) Field of Classification Search
CPC ..... A61M 5/1411; A61M 5/162; A61M 5/14; A61J 2001/201; A61J 2001/2058
USPC .......................................... 604/251, 415, 416
See application file for complete search history.

(56) References Cited

U.S. PATENT DOCUMENTS

| | | | |
|---|---|---|---|
| 356,150 | A | 1/1887 | Mower |
| 3,030,952 | A | 4/1962 | Elder |
| 3,834,386 | A | 9/1974 | Sisley |
| 4,046,276 | A | 9/1977 | Winchell et al. |
| 5,242,424 | A | 9/1993 | Chen |

(Continued)

FOREIGN PATENT DOCUMENTS

| | | |
|---|---|---|
| DE | 8913766 | 1/1990 |
| DE | 19748497 | 5/1999 |

(Continued)

*Primary Examiner* — Emily Schmidt
(74) *Attorney, Agent, or Firm* — Occhiuti & Rohlicek LLP (57) ABSTRACT

The invention relates to a drip chamber for an infusion device and an infusion device having such a drip chamber, by means of which medical solutions can be fed to a patient, such as infusion solutions for chemotherapy. The drip chamber (1) according to the invention is provided for connecting to a fastener (8) of an infusion container (2), comprising a withdrawal part (25) for withdrawing fluid, having an opening (28) closed by a penetrable membrane (27) and an injection part (26) for injecting a fluid, having an opening (30) closed by a penetrable membrane (29). The connecting part (7) and/or piercing spike (11) of the drip chamber (1) according to the invention is designed such that a snap-fit or latching connection to the injection part (13) and/or the withdrawing part (25) of the fastener (8) of the infusion container (2) can be produced when the connecting part (7) of the drip chamber (1) is connected to the fastener (8) of the infusion container (2).

16 Claims, 5 Drawing Sheets

(56) References Cited

U.S. PATENT DOCUMENTS

| | | | |
|---|---|---|---|
| 5,445,623 A | 8/1995 | Richmond | |
| 5,735,826 A | 4/1998 | Richmond | |
| 8,211,081 B2 | 7/2012 | Brandenburger et al. | |
| 2004/0002684 A1* | 1/2004 | Lopez | 604/240 |
| 2009/0054865 A1 | 2/2009 | Brandenburger | |
| 2011/0004184 A1* | 1/2011 | Proksch et al. | 604/407 |

FOREIGN PATENT DOCUMENTS

| | | |
|---|---|---|
| DE | 102006053219 | 11/2006 |
| FR | 1371072 | 8/1964 |
| JP | 2003-339821 | 12/2003 |
| JP | 2004-008633 | 1/2004 |
| JP | 2008-516707 | 5/2008 |
| WO | 01/23277 | 4/2001 |
| WO | 02/102295 | 12/2002 |
| WO | 2008/058656 | 5/2008 |
| WO | WO 2009046903 A1 * | 4/2009 |
| WO | 2009/130147 | 10/2009 |

* cited by examiner

DRIP CHAMBER FOR AN INFUSION DEVICE AND INFUSION DEVICE HAVING A DRIP CHAMBER

CROSS-REFERENCE TO RELATED APPLICATIONS

This application is the national stage application of PCT/EP2010/003038, filed on May 18, 2010, which claims the priority of German application no. 10 2009 022 417.3, filed on May 22, 2009. The contents of both applications are incorporated by reference.

The invention relates to a drip chamber for an infusion device, with which medical solutions, for example infusion solutions for chemotherapy, are fed to a patient. The invention also relates to an infusion device with a drip chamber and to an arrangement composed of an infusion container for receiving a medical liquid and of such an infusion device.

The known infusion devices have drip chambers which effectively prevent air from entering the infusion line, particularly when the infusion container runs empty.

DE 197 48 497 A1 describes an infusion device with a drip chamber and with an infusion line. The drip chamber has a substantially cylindrical housing body with a distal inlet and a proximal outlet. An attachment part for attaching the drip chamber to a closure part of an infusion container is provided at the distal inlet of the housing body. The attachment part of the drip chamber has a piercing spike which has a liquid channel and which, for attaching the drip chamber, is inserted into a pierceable part of the closure part of the infusion container. An infusion line, which can be pinched off with a roller clamp, is attached to the proximal outlet of the housing body. The infusion line has a proximal attachment piece for attachment of an infusion cannula.

The known infusion devices comprising a piercing spike have the advantage that a rapid connection to the infusion container, for example to an infusion bag, is possible. A disadvantage, however, is that there is a danger of the drip chamber coming loose from the infusion bag. Particularly in the event of sudden movements by the patient, for example when eating, drinking or walking, the piercing spike of the drip chamber can easily come loose from the pierceable part of the infusion container, with the result that the entire system is no longer tight. The consequence is an escape of the infusion solution from the infusion container. Particularly when using highly toxic medicaments, for example cytostatics, there is a danger of contamination of patients, medical personnel or visitors.

U.S. Pat. No. 5,735,826 describes an arrangement composed of an infusion container, in particular an infusion bag, and of an infusion device with a drip chamber. The infusion bag and the drip chamber each have attachment pieces that permit a needleless connection. In this way, a releasable connection is created without the danger of the drip chamber coming loose from the infusion bag during the infusion. A disadvantage, however, is that the infusion system provides special attachment pieces that do not have the piercing spikes and piercing parts that have become established in practice.

U.S. Pat. No. 356,150 discloses a drip chamber for an infusion device, which drip chamber has a screw-type closure with which the drip chamber is screwed onto an infusion container, in particular an infusion bottle. Here too, it is a disadvantage that use is not made of the established piercing spikes and piercing parts.

WO 2008/058656 A1 describes a drip chamber for an infusion device, which drip chamber has a securing part with a plurality of securing elements arranged about the circumference. The securing elements are designed in such a way that they can be spread from a position in which they engage firmly around a corresponding securing part of the infusion container to a position in which they release the securing part of the infusion container. This drip chamber also once again has a piercing spike for withdrawing the liquid from the infusion container.

US 2009/054865 A1 describes a closure cap for containers filled with medical liquids, which closure cap has a withdrawal part for withdrawing liquid and also has an injection part for injecting liquid. The withdrawal part and the injection part each have an opening closed by a pierceable membrane, wherein the membrane of the withdrawal part is pierced by a spike and the membrane of the injection part is pierced by the needle of a syringe.

It is an object of the invention to make available an easy-to-use drip chamber for an infusion device, which drip chamber permits a reliable connection of infusion device and infusion container. A further object of the invention is to make available an easy-to-use infusion device with such a drip chamber, and an arrangement that is composed of an infusion container and of such a drip chamber and that permits a reliable connection of infusion device and infusion container.

It is also an object of the invention to make available a general-purpose drip chamber for an infusion device and a general-purpose infusion device with such a drip chamber, which drip chamber and infusion device are easy to use.

According to the invention, these objects are achieved by the features of claims 1, 13 and 14. Advantageous embodiments of the invention are the subject matter of the dependent claims.

The drip chamber according to the invention is intended for attachment to a closure part of an infusion container, which has a withdrawal part for withdrawing liquid (withdrawal site), with an opening closed by a pierceable membrane, and an injection part for injecting a liquid (injection site), with an opening closed by a pierceable membrane.

The drip chamber according to the invention has an attachment part, which is attached to the closure part of the infusion container. A housing body having a distal inlet and a proximal outlet is integrally formed on the attachment part. A piercing spike with a liquid channel is attached to the distal inlet of the housing body and is inserted into the pierceable membrane that closes the opening of the withdrawal part of the closure part of the infusion container.

The attachment part and/or the piercing spike of the drip chamber according to the invention is designed in such a way that a snap-fitting or latching connection to the injection part and/or to the withdrawal part of the closure part of the infusion container can be produced when the attachment part of the drip chamber is attached to the closure part of the infusion container. This ensures a reliable connection between the attachment part of the drip chamber and the closure part of the infusion container. An additional securing part, for example having a plurality of clips engaging around the closure part of the infusion container, is therefore not necessary. The attachment part of the drip chamber is secured solely by means of the attachment part of the drip chamber being placed onto the closure part of the infusion container. Since the drip chamber is secured on the closure part of the infusion container, the piercing spike of the drip chamber cannot slip out of the membrane with which the opening in the withdrawal part of the closure part of the infusion container is closed. Therefore, compared to the known drip chambers, the piercing spike can be kept relatively short. Whereas the relatively long piercing spike of the known drip chambers can break off if not properly handled, this risk is minimal with the relatively short piercing spike of the drip chamber according to the invention. Moreover, the relatively short piercing spike can be better introduced into the withdrawal site. The risk of injury is also less.

The drip chamber according to the invention is intended to be attached to the closure part of an infusion container that not only has a withdrawal part for withdrawing liquid, but also an injection part for injecting liquid, in particular a medicament, into the infusion container. Therefore, in a preferred embodiment, the drip chamber according to the invention can be used not only to withdraw liquid, but also to inject a liquid, in particular a medicament. This preferred embodiment is characterized in that the securing part is designed as an injection part. The medicament can therefore also be injected via the injection part of the attachment part of the drip chamber when the drip chamber is attached to the closure part of the infusion container.

Even if the securing part is not designed as an injection part, the closure cap according to the invention can serve as a cover for the injection site, such that there is no danger of contamination.

In a preferred embodiment, the securing part of the attachment part of the drip chamber has a cylindrical projection, which can be plugged with a latching or snap-fitting action into the opening of the injection part of the closure part of the infusion container, such that the attachment part of the drip chamber is secured safely on the closure part of the infusion container. If the attachment part is designed as an injection part, the cylindrical projection is a hollow cylindrical projection through which the needle of the syringe can be guided.

The cylindrical or hollow cylindrical projection of the securing part of the attachment part of the drip chamber preferably has a locking element which, when the attachment part is attached to the closure part of the infusion container, engages behind a projection provided on the opening of the injection part of the closure part. The projection engaging behind the projection of the injection part of the closure part of the infusion container is preferably a circumferential edge, which protrudes outward from the cylindrical projection of the injection part of the attachment part. Instead of only one locking element, however, it is also possible for several locking elements to be provided on the cylindrical projection of the securing part. These locking elements can also be designed as grooves into which corresponding projections of the closure part of the infusion container engage with a latching or snap-fitting action.

In an alternative embodiment, it is not only the injection part but also the piercing spike that is designed as a securing part for holding the attachment part of the drip chamber firmly on the closure cap of the infusion bottle. In this embodiment, the piercing spike preferably has, on the upper portion, a groove or undercut, while the withdrawal part of the closure part of the infusion container has a corresponding projection that engages with a snap-fitting or latching action in the groove or undercut of the piercing spike when the attachment part of the drip chamber is placed onto the closure part of the infusion container. Instead of a groove or undercut on the piercing spike and a projection on the closure part, it is also possible to provide a projection on the piercing spike and a groove or undercut on the closure part. It is preferable to provide a circumferential groove or undercut and a circumferential projection. However, it is also possible to provide a plurality of grooves or undercuts and projections distributed about the circumference. It is important simply that a latching or snap-fitting connection is produced. In the alternative embodiment, the securing part preferably designed as an injection part can be omitted in principle. However, particularly reliable locking can be achieved using both securing parts.

The injection part of the attachment part of the drip chamber preferably has an annular projection, in which is arranged the membrane with which the opening of the injection part is closed. The membrane of the injection part is thus safely held in the annular projection of the attachment part.

The attachment part of the drip chamber can be differently designed. In a preferred embodiment, the attachment part is designed as a cap-shaped attachment part having a cover part and an edge part. In this way, the attachment part can be handled like a conventional closure cap.

The housing body and the securing part, which is preferably designed as an injection part, are preferably arranged lying next to each other on the cover part of the cap-shaped attachment part, such that the injection part is easily accessible.

The infusion device according to the invention comprises the drip chamber according to the invention and an infusion line which is to be attached to a patient and which is attached to the proximal outlet of the housing body of the drip chamber.

The arrangement according to the invention is composed of an infusion container for receiving a medical liquid and of such an infusion device. The infusion container can be an infusion bag or a receptacle. The infusion container can, for example, be a bottle made of glass or plastic. The closure part of the infusion container according to the invention is characterized in that the closure part has a withdrawal part and also an injection part, each having an opening closed by a pierceable membrane. When the drip chamber according to the invention is placed onto the infusion container according to the invention, the membrane of the withdrawal part is pierced by the piercing spike of the drip chamber. The securing part, preferably designed as an injection part, of the attachment part of the drip chamber and the injection part of the closure part of the infusion container are arranged in such a way that both injection parts face each other when the attachment part of the drip chamber is placed onto the closure part of the infusion container. It is therefore possible to pierce the membrane of both injection parts using the needle of a syringe, in order to inject a liquid, for example a medicament.

The closure part of the infusion container is preferably designed as a closure cap with a cover part and an edge part, such that the likewise cap-shaped attachment part of the drip chamber can be placed with a matching fit onto the cover part of the closure cap of the infusion container.

In a preferred embodiment, the closure cap of the infusion container has a mounting part onto which the cover part of the attachment part of the drip chamber is placed. This mounting part can have a circular or non-circular cross section, preferably an oval cross section, such that the attachment part of the drip chamber can be secured against rotation on the mounting part of the cover part of the closure cap.

Illustrative embodiments of the invention are explained in more detail below with reference to the drawings, in which.

Figure 1:
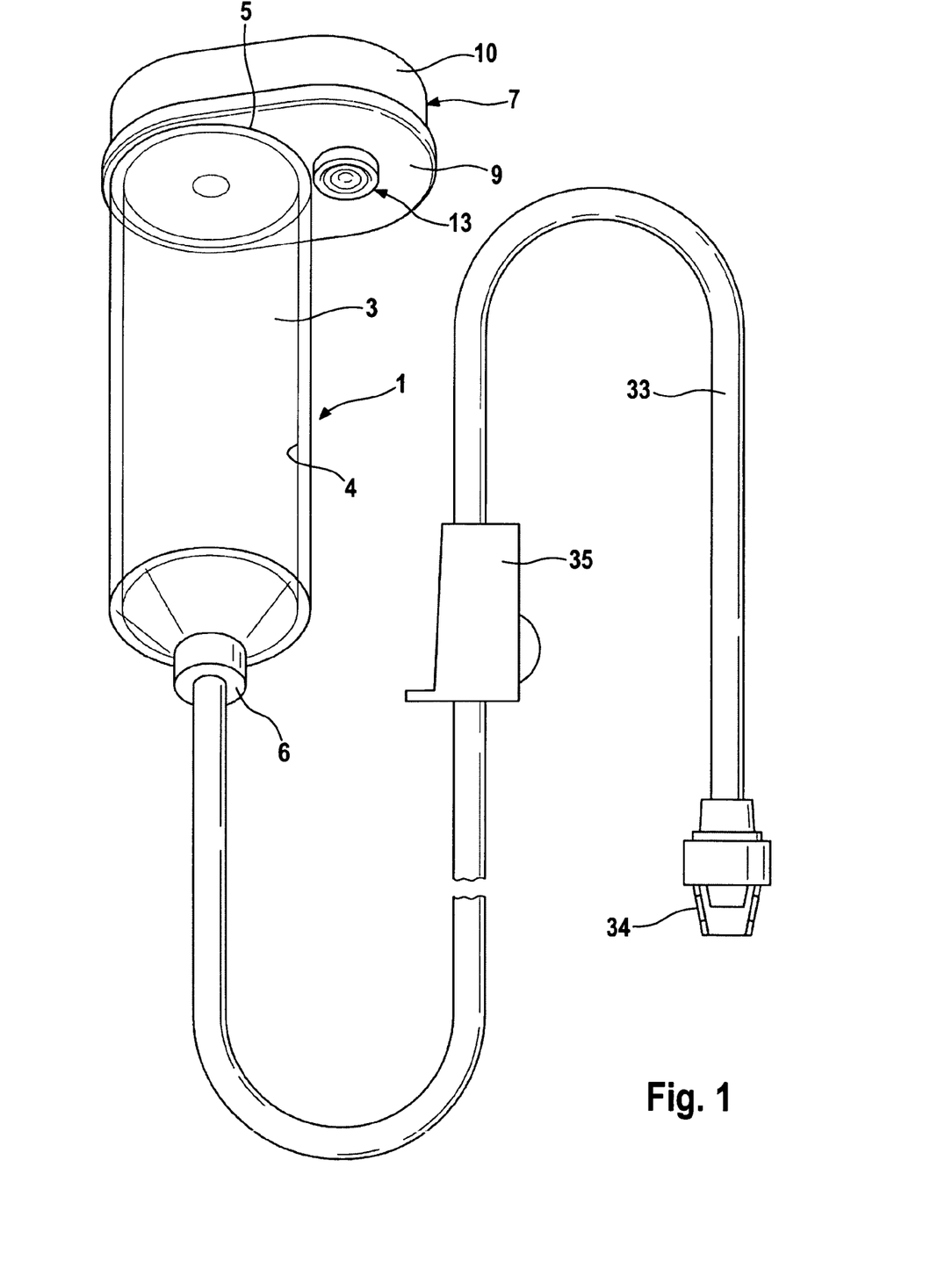
FIG. 1 shows an infusion device according to the invention with a drip chamber according to the invention.
Figure 2:
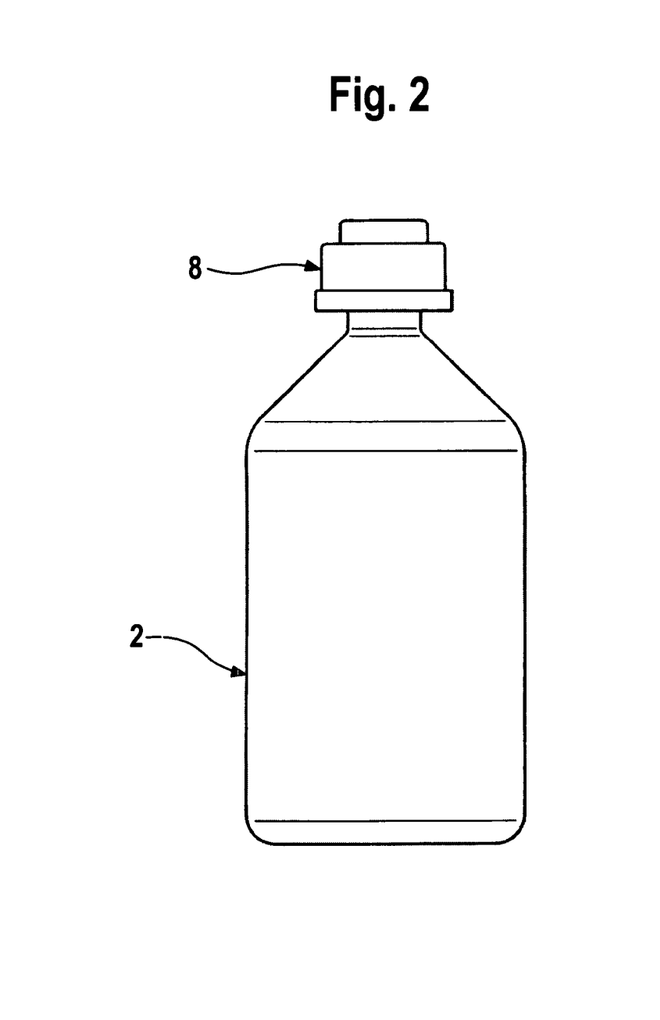
FIG. 2 shows an infusion container with a closure part according to the invention, to which the attachment part of the drip chamber of the infusion device according to the invention is attached.

FIG. 1 shows an infusion device according to the invention, which comprises the drip chamber 1 according to the invention, while FIG. 2 shows an infusion container 2 to which the drip chamber 1 of the infusion device from FIG. 1 is attached.

The drip chamber 1 of the infusion device according to the invention has an elongate housing body 3 which is made of transparent plastic and which surrounds a chamber 4. The housing body 3 has a distal inlet 5 and a proximal outlet 6. In the position of use, the drip chamber 1 is arranged in such a way that the distal inlet 5 lies at the top and the proximal outlet 6 at the bottom.

Figure 3:
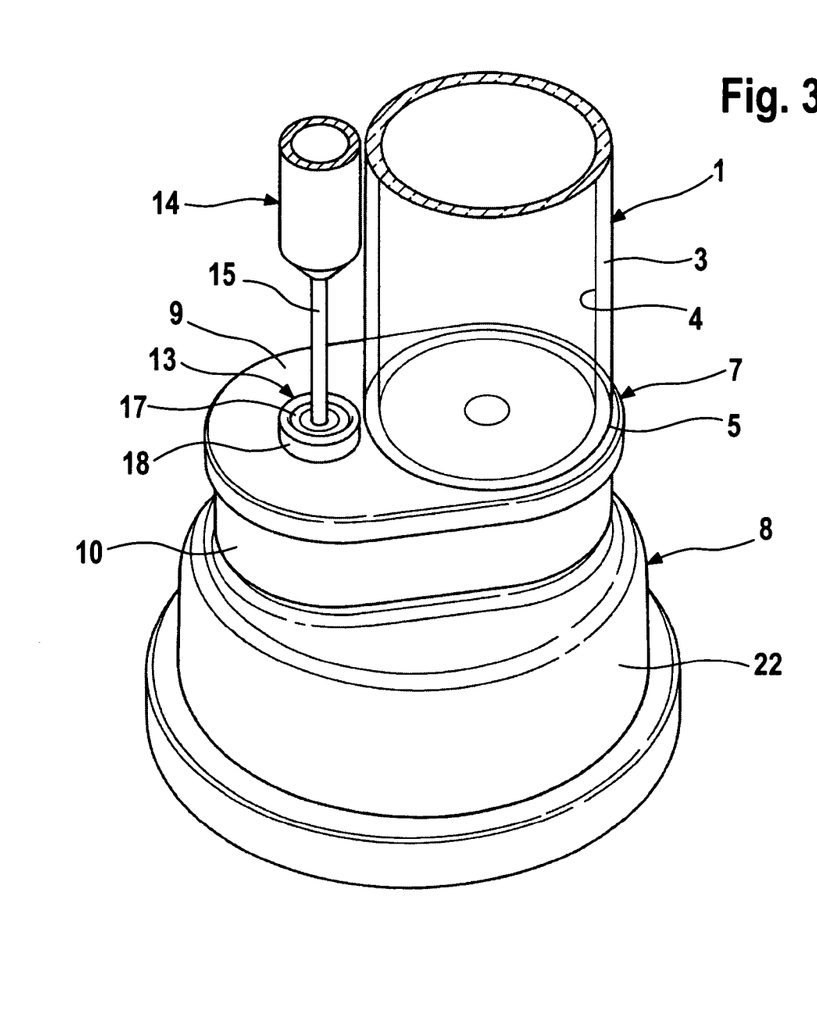
FIG. 3 shows a perspective view of the drip chamber and of the closure part of the infusion container.
Figure 4:
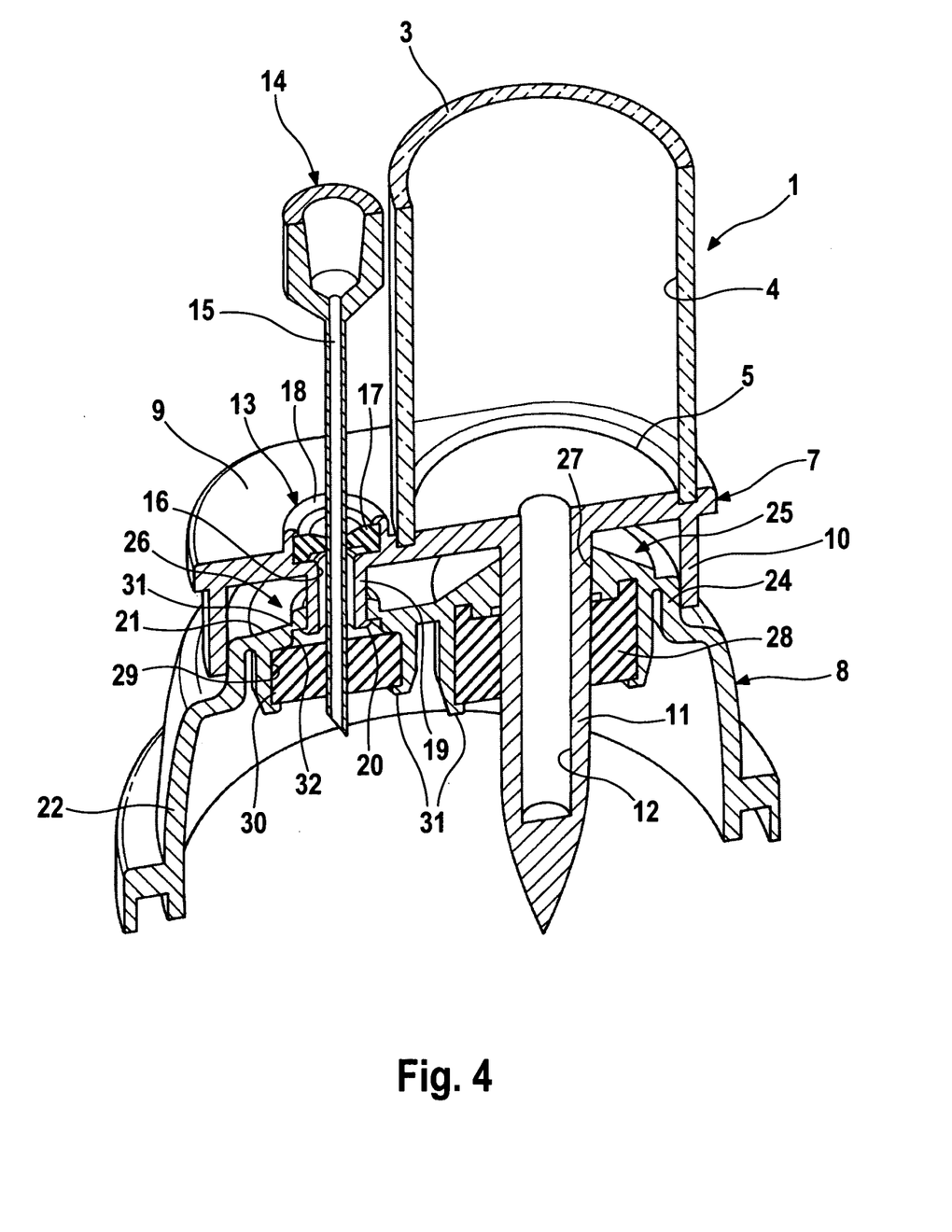
FIG. 4 shows a cross section through the drip chamber and the closure part from FIG. 3.

The drip chamber 1 has an attachment part 7 for attaching the drip chamber to a closure part 8 of the infusion container 2. In the present illustrative embodiment, the infusion container 2 is an infusion bottle made of glass or plastic and closed by the closure part 8. The closure part 8 of the infusion container 2 is designed as a closure cap in the present illustrative embodiment. The attachment part 7 of the drip chamber 1 is also designed as a cap-shaped attachment part that can be placed onto the closure cap 8 of the infusion bottle 2 with a matching fit. FIGS. 3 and 4 show perspective views of the drip chamber 1, which is attached by the attachment part 7 to the closure cap 8 of the infusion bottle 2.

The cap-shaped attachment part 7 of the drip chamber 1 has a cover part 9 and an edge part 10. In the present illustrative embodiment, the cap-shaped attachment part 7 has a non-circular cross section, in particular an oval cross section. The housing body 3 of the drip chamber 1 is connected firmly to the cover part 9 of the attachment part 7. The housing body 3 and the cover part 9 are here separate parts, which are bonded or welded to each other. However, the housing body and the cover part can also be designed in one piece.

The cover part 9 of the attachment part 7 closes the distal inlet 5 of the housing body 3. A piercing spike 11, which has a liquid channel 12, is formed integrally on the cover part 7 above the distal inlet 5 of the housing body 3. In addition to the liquid channel, the piercing spike 11 can also have an air release channel. The housing body 3 and the piercing spike 11 are arranged eccentrically on the cover part 9 of the attachment part 7, and the piercing spike 11 extends only a short distance beyond the edge part 10 of the cover part 9.

In addition to the housing body 3, an injection part 13 is provided on the cover part 9 of the attachment part 7. The housing body 3 and the injection part 13 lie closely adjacent to each other. The injection part 13 permits the injection of a liquid, in particular of a medicament, with a syringe 14, which is merely indicated symbolically in FIG. 4 and which has a needle 15. The injection part 13 is designed as it were as a securing part with which the attachment part 7 of the drip chamber 1 is secured on the closure part 8 of the infusion container 2.

The injection part 13 has an opening 16 in the cover part 9 of the attachment part 7, which opening 16 is closed tightly by a pierceable and self-sealing membrane 17. The membrane 17 sits clamped in an annular projection 18, which is integrally formed on the outside of the cover part 9 of the attachment part 7. Integrally formed on the inside of the cover part 9 and opposite the membrane 17, there is a hollow cylindrical projection 19 with a locking element 20 which, when the drip chamber 1 is attached to the infusion container 2, secures the attachment part 7 of the drip chamber 1 to the closure part 8 of the infusion container 2 with a latching or snap-fitting action. The locking element is an outwardly protruding circumferential edge 20 at the end of the hollow cylindrical projection 19.

The closure cap 8 of the infusion container 2 has a cover part 21 and an edge part 22. The edge part 22 has an upper mounting part 24 which, in the present illustrative embodiment, has a non-circular cross section, in particular an oval cross section. The oval mounting part 24 of the closure cap 8 of the infusion bottle 2 is designed in such a way that the oval edge part 10 of the attachment part 7 of the drip chamber 1 can be placed with a matching fit onto the upper mounting part 24.

On the cover part 21 of the closure cap 8 of the infusion bottle 2 there are a withdrawal part 25 for withdrawing a liquid, in particular an infusion solution, and an injection part 26 for injecting a liquid, in particular a medicament, and these are arranged alongside each other at the same spacing as the piercing spike 11 and the injection part 13 of the drip chamber 1.

The withdrawal part 25 has an opening 27, which is closed by a pierceable self-sealing membrane 28, and the injection part 26 has an opening 29, which is closed by a pierceable self-sealing membrane 30. The membranes 28, 30 of the withdrawal part 25 and of the injection part 26 are held with a clamping action by inwardly extending projections 31 formed integrally on the cover part 21 of the closure cap 8.

The injection part 26 of the closure cap 8 is designed as a receiving piece for the hollow cylindrical projection 19 of the attachment part 7, into which the hollow cylindrical projection can be inserted with a latching or snap-fitting action. In doing so, the circumferential edge 20 on the hollow cylindrical projection 19 engages behind an annular projection 31 provided on the opening of the injection part 26 in a cylindrical recess 32 between the inside of the cover part 21 and the membrane 30.

When the drip chamber 1 is attached to the infusion bottle 2, it is possible to withdraw the liquid, in particular infusion solution, located in the bottle. A liquid, in particular a medicament, can likewise be injected using a syringe 14. For this purpose, the membrane 17 of the injection part 13 of the drip chamber 1 and the membrane 30 of the injection part 26 of the closure cap 8 are pierced by the needle 15 of the syringe 14, the needle then extending through the hollow cylindrical projection 19 of the attachment part 7. The injection site of the drip chamber represents a protection against contamination or contact.

Since the attachment part 7 of the drip chamber 1 is locked with the hollow cylindrical projection 19 on the closure cap 8 of the infusion bottle 2, the attachment part 7 of the drip chamber 1 cannot easily be detached from the closure cap 8 of the infusion bottle 2, for example by sudden movements of the patient, and the piercing spike slip out of the withdrawal part of the infusion bottle. However, since the connection of drip chamber and infusion bottle is a snap-fitting or latching connection, the drip chamber can be released again at any time from the infusion bottle. For this purpose, however, a certain force has to be applied.

As long as the attachment part of the drip chamber sits on the closure cap of the infusion bottle, the drip chamber itself constitutes a closure cap, which protects the withdrawal part and the injection part.

In addition to the drip chamber 1, the infusion device according to the invention comprises an infusion line 33, which is attached to the proximal outlet 6 of the drip chamber. Located at the proximal end of the hose line 33 is a connection piece 34, for example a Luer lock connector, for the attachment of a cannula. A conventional hose clamp 35 is provided on the infusion line 33 in order to interrupt the infusion (FIG. 1). Since the drip chamber and the infusion bottle are securely connected to each other, the length of the piercing spike can be relatively short, with the result that the piercing spike does not in principle have to extend beyond the edge part of the attachment part. In this way, injuries can be avoided.

Figure 5:
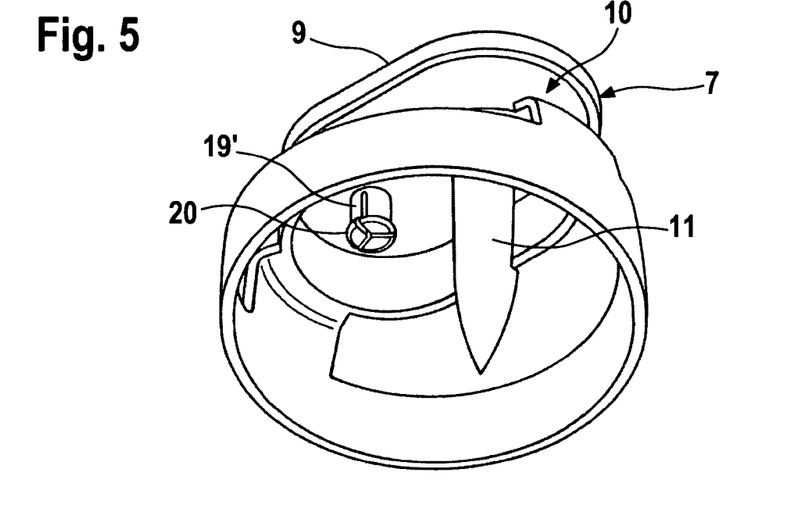
FIG. 5 shows an alternative embodiment of the drip chamber according to the invention.
Figure 6:
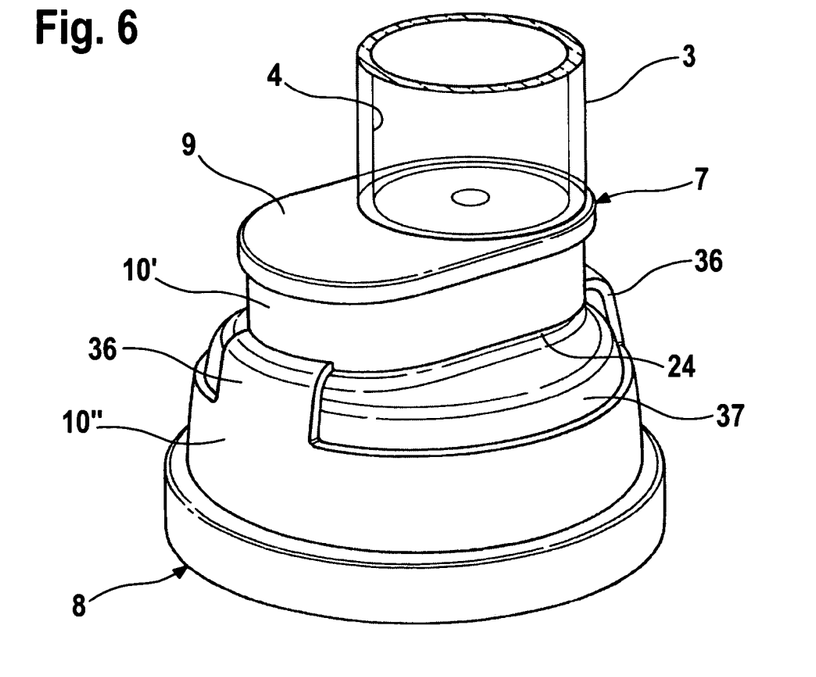
FIG. 6 shows the drip chamber from FIG. 5 and the corresponding closure part of the infusion container.

FIGS. 5 and 6 show an alternative embodiment of the closure cap and of the drip chamber. This embodiment differs from the illustrative embodiment described with reference to FIGS. 1 to 4 in that, on the one hand, the drip chamber does not have an injection part for injecting a liquid, in particular a medicament. Therefore, in this embodiment, it is not possible to inject a liquid when the drip chamber is secured on the infusion bottle. On the other hand, the embodiment in FIGS. 5 and 6 differs from the illustrative embodiment in FIGS. 1 to 4 in the design of the edge part of the attachment part of the drip chamber. Since there are no further differences, reference is made to the description of the embodiment in FIGS. 1 to 4, and the parts corresponding to one another are designated by the same reference numbers.

In the alternative embodiment, instead of the hollow cylindrical projection, a solid cylindrical projection 19' is integrally formed on the underside of the cover part 9 of the attachment part 7 and serves as a protective cap that closes the opening of the injection part 26 of the closure cap 8. The cylindrical projection 19' in the alternative embodiment does not have to be a hollow cylinder since, in the absence of the injection part, the needle of a syringe is not introduced through the projection. At its end, the cylindrical projection 19' once again has, as a locking element, a circumferential edge 20 that engages behind the annular projection in the receiving piece of the closure cap when the attachment part of the drip chamber is placed onto the closure cap. The cylindrical projection 19' can be composed of a plurality of resilient portions so as to be able to produce a snap-fitting or latching connection.

In the alternative embodiment, the edge part 10 of the attachment part 7 of the drip chamber 1 has an oval upper edge part 10' and a circular lower edge part 10", wherein the upper and lower edge parts 10', 10" are connected to each other via two opposite webs 36. While the upper edge part 10' of the attachment part 7 sits on the oval mounting part 24 of the edge part 22 of the closure cap 8, the lower edge part 10" of the attachment part 7 sits on the circular lower portion 37 of the edge part 22 of the closure cap. In this way, the drip chamber acquires an additional hold on the infusion bottle.

It is obvious that the alternative embodiment of the drip chamber can also have a piercing part in order to be able to inject a liquid, in particular a medicament, when the drip chamber is connected to the infusion bottle.

Figure 7:
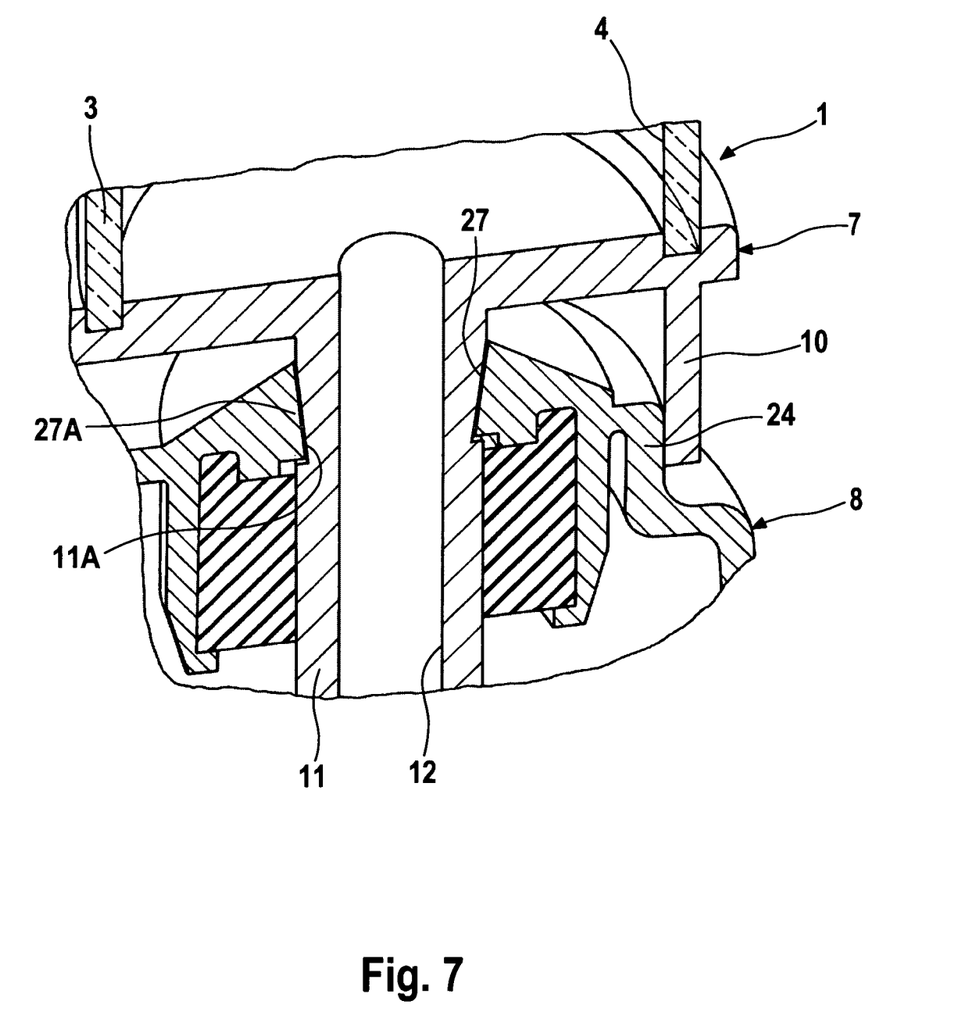
FIG. 7 shows a partial view of another alternative embodiment of the drip chamber in a perspective representation.

FIG. 7 shows a partial view of another alternative embodiment of the drip chamber in a partially sectioned representation. The drip chamber in FIG. 7 differs from the embodiment described with reference to FIGS. 1 to 4 in that the piercing spike 11 is also secured with a latching or snap-fitting action on the closure cap 8 of the infusion bottle 2. Thus, the piercing spike 11 also represents a securing part that holds the attachment part 7 of the drip chamber firmly on the closure cap 8 of the infusion bottle. The corresponding parts are once again provided with the same reference signs.

In the alternative embodiment, the securing part in the form of the cylindrical projection 19, 19' can in principle be omitted. However, particularly secure blocking can be achieved with both securing parts 19, 19' and 11.

In the alternative embodiment, the piercing spike 11 has, on the upper portion, a groove or undercut 11A, while the withdrawal part 25 of the closure part 8 of the infusion container 2 has, in the area of the opening 27, a corresponding projection 27A, which engages with a snap-fitting or latching action in the groove or undercut of the piercing spike 11 when the attachment part 7 of the drip chamber is placed onto the closure part 8 of the infusion container and the piercing spike 11 is pushed forward into the opening 27 of the withdrawal part 25.

The invention claimed is:

1. A drip chamber for an infusion device for attachment to a closure part of an infusion container, which has a withdrawal part for withdrawing liquid, with an opening closed by a pierceable membrane, and an injection part for injecting a liquid the injection part having an opening closed by a pierceable membrane, wherein the drip chamber comprising:

an attachment part, which can be attached to the closure part of the infusion container, a housing body, which is connected to the attachment part and has a distal inlet and a proximal outlet, a piercing spike, which is attached to the distal inlet of the housing body and can be inserted into the pierceable membrane of the withdrawal part of the closure part of the infusion container, wherein the attachment part includes a cylindrical projection having a locking element which, when the attachment part is attached to the closure part of the infusion container, engages behind a projection provided on the opening of the injection part of the closure part, wherein the cylindrical projection is configured to be plugged with a latching or snap-fitting action into the opening of the injection part of the closure part of the infusion container.

2. The drip chamber as claimed in claim 1, wherein the locking element is a circumferential edge, which protrudes outward from the cylindrical projection of the attachment part.

3. The drip chamber as claimed in claim 1, wherein the injection part of the attachment part has an annular projection in which is arranged the membrane with which the opening of the injection part is closed.

4. The drip chamber as claimed in claim 1, wherein the piercing spike of the attachment part has a groove or undercut into which a projection of the withdrawal part of the closure part of the infusion container can engage with a latching or snap-fitting action.

5. The drip chamber as claimed in claim 1, wherein the attachment part is designed as a cap-shaped attachment part having a cover part and an edge part.

6. The drip chamber as claimed in claim 5, wherein the edge part of the attachment part has a circular or oval cross section.

7. An infusion device with a drip chamber as claimed in claim 1 and with an infusion line which is to be attached to a patient and which is attached to the proximal outlet of the housing body of the drip chamber.

8. The drip chamber as claimed in claim 5, wherein the closure part of the infusion container is designed as a closure cap with a cover part and an edge part, wherein the edge part of the cap-shaped attachment part of the drip chamber can be placed with a matching fit onto the cover part of the closure cap of the infusion container.

9. The drip chamber as claimed in claim 8, wherein the cover part of the closure cap of the infusion container has a mounting part onto which the cap-shaped attachment part of the drip chamber can be placed with a matching fit.

10. The drip chamber as claimed in claim 9, wherein the mounting part of the cover part of the closure cap of the infusion container has a circular or oval cross section.

11. The drip chamber as claimed in claim 1, wherein the attachment part has a securing part, the securing part being configured as an injection part for injecting a liquid, said injection part having an opening closed by a pierceable membrane.

12. The drip chamber as claimed in claim 11, wherein the injection part of the closure part of the infusion container is designed as a receiving piece that receives a projection of a securing part of the attachment part of the drip chamber with a latching or snap-fitting action.

13. The drip chamber as claimed in claim 1, wherein the attachment part has a securing part, the securing part including a snap-fitting or latching connection to the injection part of the closure part of the infusion container when the attachment part is attached to the closure part of the infusion container.

14. The drip chamber as claimed in claim 1, wherein the piercing spike is configured as a securing part in such a way that a snap-fitting or latching connection to the withdrawal part of the closure part of the infusion container can be produced when the attachment part is attached to the closure part of the infusion container.

15. An arrangement composed of an infusion container for receiving a medical liquid and of an infusion device as claimed in claim 7, wherein the infusion container has a closure part with a withdrawal part, which has an opening closed by a pierceable membrane into which the piercing spike of the drip chamber can be inserted, and an injection part for injecting a medicament, which injection part has an opening closed by a pierceable membrane.

16. The arrangement as claimed in claim 15, wherein the withdrawal part of the closure part of the infusion container is designed as a receiving piece that receives the piercing spike of the attachment part of the drip chamber with a latching or snap-fitting action.

* * * * *